United States Patent [19]

Svensson et al.

[11] Patent Number: 4,638,065
[45] Date of Patent: Jan. 20, 1987

[54] CRYSTALLIZATION METHOD FOR HMX AND RDX

[75] Inventors: Leif Svensson; Jan-Olof Nyqvist, both of Karlskoga; Lars Westling, Stengungssund, all of Sweden

[73] Assignee: Aktiebolaget Bofors, Bofors, Sweden

[21] Appl. No.: 716,066

[22] Filed: Mar. 26, 1985

[30] Foreign Application Priority Data

Apr. 4, 1984 [SE] Sweden ............................... 8401857

[51] Int. Cl.$^4$ ................... C07D 251/59; C07D 225/02
[52] U.S. Cl. .................................... 544/196; 540/475
[58] Field of Search ................. 260/239 HM; 544/196

[56] References Cited

U.S. PATENT DOCUMENTS 2,434,230 6/1948 Schiessler et al. .................. 260/248
2,656,355 10/1953 Bachmann ........................... 260/248
2,959,587 11/1960 Johnson et al. ..................... 260/248

FOREIGN PATENT DOCUMENTS 816157 6/1969 Canada ........................ 260/239 HM
7214112 5/1969 Japan ........................... 260/239 HM

OTHER PUBLICATIONS

I&EC Product Research and Development 4, 1965 by George, et al., "Solvates of Octahydro-1,3,5,7-tetranitro-1,3,5,7-tetrazocine (HMX)", pp. 209-214.

Primary Examiner—Richard L. Raymond
Assistant Examiner—D. B. Springer
Attorney, Agent, or Firm—Pollock, Vande Sande & Priddy

[57] ABSTRACT

The present invention relates to a method for the recrystallization of the high explosives HMX and RDX. According to the invention, the explosive is dissolved in a low molecular weight, liquid (at room temperature) lactone, after which the degree of saturation of the solution obtained, is changed by either lowering the temperature or by diluting with water.

This method produces, depending on the crystallization method chosen, β-HMX crystals or RDX crystals of either 50–1500 μm or 5–50 μm median particle diameter respectively.

10 Claims, No Drawings

CRYSTALLIZATION METHOD FOR HMX AND RDX

The present invention relates to a method for the recrystallization of the high explosives HMX and RDX. There are several reasons why these explosives need to be recrystallized and several methods for this have been examined previously.

HMX, or octahydro-1,3,5,7-tetranitro-1,3,5,7-tetrazocine, occurs in four different crystal modifications, two of which, α and β, can be readily obtained. Of these two, β is the desirable one, since it has the highest density and the lowest sensitivity. The crystal modification which is obtained, depends largely upon the conditions used for the crystallization. Furthermore, the crystal modification which is obtained is largely determined by which solvent is used. As examples of the solvents which are at present used for recrystallizing HMX, and which are known to give negligible amounts of α-HMX crystals, can be mentioned acetone and cyclohexanone, both of which have low solubility for HMX.

Crystallized HMX is normally used for the production of mixed explosives, together with trinitrotoluene, and in wax- and polymer-coated HMX-charges. Within both of these charge types the highest possible degree of packing for the HMX is desirable, which means that one must have HMX-crystals of different sizes available. Therefore, at the recrystallization of HMX, one must concentrate either on preparing directly HMX crystals with a specific particle size distribution or on preparing recrystallized HMX batchwise with different median particle sizes and mix these to obtain the desired particle size distribution. As far as we know, no one has yet succeeded in preparing crystallized HMX on a production scale with an ideal particle size distribution. Therefore, one has previously been forced to utilize the second method, mixing two or more products, each with its own narrow particle size distribution.

The method according to the invention certainly does not allow a direct preparation of HMX with an ideal particle size distribution either, but it can, simply by the choice of crystallization method and without any other change in the method, be used to obtain crystals with reproducible median particle sizes.

RDX, or hexahydro-1,3,5-trinitro-1,3,5-triazine, generally must also be recrystallized after the synthesis in order to obtain purer crystals and/or other crystal sizes. RDX can form two different polymorphic forms; the less common of these has only been isolated in small quantities under special conditions. The other form, which is the one formed at production scale, can, depending on the solvent used, form either needle-like, flat or more spherical crystals. During the recrystallization of RDX according to the invention the most desirable, spherical crystal shape is obtained.

The present invention thus relates to a new method for recrystallizing HMX and RDX based on the use of a special type of solvent. According to the invention, the crude HMX or RDX is dissolved in a low molecular weight, liquid (at room temperature) lactone possessing four or more carbon atoms in the ring part, such as γ-butyrolactone, γ-valerolactone, δ-valerolactone or ε-caprolactone.

Alternative solvents according to the invention

γ-butyrolactone 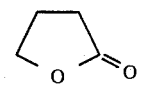 (1)

γ-valerolactone 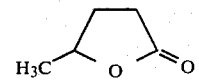 (2)

δ-valerolactone 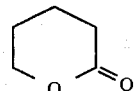 (3)

ε-caprolactone 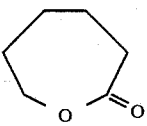 (4)

Of these, γ-butyrolactone is the most economically attractive solvent. Due to its better solubility for HMX and RDX, it has a much greater capacity compared to cyclohexanone.

The particular advantage with this solvent is that its solubility for HMX and RDX is strongly temperature dependant. This gives the solvent a pronounced higher capacity compared to the solvents used previously. In addition the possibilities exist, both for HMX and RDX, to reproducibly select the particle size by the choice of crystallization method.

TABLE 1

The solubility of HMX in some lactones

| Solvent | Amount of HMX (g) dissolved in 100 g solvent | |
|---|---|---|
| | 23° C. | 120° C. |
| γ-butyrolactone | 11.0 | 48.1 |
| γ-valerolactone | 9.2 | 35.5 |
| δ-valerolactone | 6.5 | 35.7 |
| ε-caprolactone | 6.8 | 38.3 |

TABLE 2

Some comparative values for the solvents used previously

| Solvent | Amount of HMX (g) dissolved in 100 g solvent | | |
|---|---|---|---|
| | 20° C. | 40° C. | 100° C. |
| cyclohexanone | 2.5 | 3.5 | 7.0 |
| acetone | 2.0 | 3.8 | — |

For γ-butyrolactone, the diagram shows the solubility curve for both HMX and RDX.

Additional advantages with γ-butyrolactone as a solvent for HMX are that it gives no detectable amount of α-HMX and that the result is not affected by any residual acetic acid in the crude explosive. Furthermore γ-butyrolactone has a low toxicity and can be reused several times in the process before it has to be redistilled.

Generally the acid content can be allowed to rise to 8-10% before the γ-butyrolactone has to be repurified by distillation of the acetic acid and water.

The well-known ability of HMX to form complexes with other compounds does not give rise to any real problems during the recrystallization from γ-butyrolactone. Complex formation can occur between HMX and γ-butyrolactone, but no traces of the complex can be detected after a careful water wash. The product is of good crystal shape. However, it is essential that the HMX crystals obtained are thoroughly sucked dry before washing with water since otherwise the HMX can be precipitated from the remaining solvent during the water wash. We have performed several experiments to ascertain when HMX forms a complex with γ-butyrolactone and how this complex behaves under certain conditions. It has been shown that the complex is formed at low water and/or acetic acid concentrations viz. the complex is formed at up to 5% water, or 3% water plus 3% acetic acid. With 4% water plus ≧4% acetic acid pure β-HMX is obtained. In the normal case it is therefore possible that the complex is formed during the crystallization and that it is decomposed upon filtration or washing with water.

A number of experiments has also been performed to demonstrate when the complex is decomposed. These experiments gave the following results: when the crystals which had separated from a γ-butyrolactone solution were filtered off under nitrogen, complexes were found to be present, whereas filtered and water washed crystals were found to contain only pure β-HMX. The same result was obtained when the crystals from the crystallization were suspended in water.

In the above mentioned experiments, the presence or absence of a complex was determined by differential scanning calorimetry. The concentration of γ-butyrolactone in the crystals was analysed by gas chromatography. The ratio of solvent to HMX (mole/mole) in the crystallized sample before washing with water, was between 0.54 and 0.85 when the complex was formed, and between 0.01 and 0.03 when it was not. After washing with water, the solvent content was less than 0.01%.

As is already known, RDX has a much lower tendency to form complexes than HMX, and consequently complex formation is no problem during the crystallization of RDX.

As mentioned earlier, the method according to the invention, gives the possibility to prepare HMX crystals, as well as RDX crystals, with different median particle sizes. This is done by the choice of crystallization method. Cooling crystallization and precipitation crystallization respectively of HMX (or RDX) dissolved in some of the above mentioned lactones gives different crystal sizes. In addition, the crystal sizes obtained under the same conditions vary very little from batch to batch.

In cooling crystallization of HMX dissolved in γ-butyrolactone, the solution is heated to 110°–120° C. and the temperature is then lowered with continuous stirring to between +20° C. and −10° C. during which the HMX is obtained as crystals with a median particle diameter of 50–1500 μm. The particle diameter can be influenced by the initial degree of saturation of the solution, the speed at which the lowering of the temperature is performed, and to a lesser extent by variations in the stirring.

Standard methods of seeding of the crystal separation can be utilized with advantage during cooling crystallization in γ-butyrolactone of both HMX and RDX.

In precipitation crystallization, the product is precipitated from a γ-butyrolactone-HMX solution by either adding water, or the converse, in a water/γ-butyrolactone ratio between 1 and 3. The precipitated crystals have a median particle diameter of 5–50 μm. In this case the crystal size is mainly dependant upon the degree of saturation of the starting solution and how fast the saturation is broken by mixing with water or vice versa. The amount of precipitated HMX depends upon the water/γ-butyrolactone ratio. A ratio of 3 gives almost complete precipitation of HMX.

Crude HMX contains some water and acetic acid and, after suspending the HMX in the lactone, these should at least partially be distilled off before the crystallization is started. Otherwise the solvent capacity of the lactone will be diminished too much. The solubility of HMX in γ-butyrolactone containing 6% acetic acid and 1% water is 9.4% at 23° C. and 28.1% at 120° C. cf. Table 1. As has been mentioned earlier, the same principles may be applied to the recrystallization of RDX.

The method of recrystallizing HMX or RDX according to this invention is based upon the use of a low molecular weight, liquid (at room-temperature) lactone as the solvent for the explosive, which is then forced to crystallize either by cooling crystallization or by precipitation with water. Among the advantages of the method according to the invension can be mentioned that the solvent is not affected by the presence of water or up to 8 to 10% acetic acid from poorly washed crude HMX and that the median particle diameter of the separated crystals can be influenced by the choice of crystallization method.

The method according to the invension has been defined in the following claims, and will now be further illustrated in the following examples.

EXAMPLE 1

105 g of HMX was mixed with 270 ml (305 g) of γ-butyrolactone and heated to 120° C. The resulting solution was cooled as fast as possible to +10° C. At 30° C. crystals seeds started to form. The crystallized product was sucked as dry as possible and was then washed with water. The median particle diameter obtained was about 70 μm.

EXAMPLE 2

To 200 l of γ-butyrolactone was added 70 kg of crude HMX with an acetic acid content of 5%. The mixture was heated to 120° C. and most of the water and acetic acid was distilled off whereupon the explosive was totally dissolved. When 120° C. had been reached the cooling crystallization was commenced. The rate at which the temperature was lowered was varied between 0.1° C./min at the beginning of the crystallization and 1° C./min at the end of the crystallization. The cooling was discontinued at 9° C. and the solid was filtered off. With such a cooling programme class 3 HMX (according to MIL-H-45444) with a median particle diameter of 300–350 μm was obtained.

EXAMPLE 3

200 ml of a saturated solution of HMX in γ-butyrolactone (20° C.) was mixed, as rapidly as possible, with 600 ml water using vigorous stirring. The precipitated product was sucked dry and was then washed with water. The median particle size was about 10 μm.

EXAMPLE 4

400 ml of water was added dropwise to 200 ml of a saturated solution of HMX in γ-butyrolactone at 20° C. with vigorous stirring. After filtration and washing with water, a product with a median particle diameter of 25–35 μm was obtained.

EXAMPLE 5

90 g of RDX was dissolved in 97 ml (110 g) of γ-butyrolactone at 120° C. The solution was cooled with stirring to 20° C. during 80 minutes. The resulting product was sucked as dry as possible, was thoroughly washed with water and then dried. The median particle diameter of the crystals was 250 μm.

EXAMPLE 6

30 g of HMX was dissolved in 100 ml (105 g) γ-valerolactone at 120° C. The resulting solution was cooled to 20° C. during 90 min., filtered and washed with water. The median particle size of the crystals was 145 μm.

What we claim is:

1. A process for recrystallizing the high explosives HMX and RDX, in which crystals of the starting explosive are dissolved in a low molecular weight, liquid (at room temperature) lactone with 5 or 6 carbon atoms in the ring, after which the degree of saturation of the solution obtained is changed in order to form new crystals of the explosive.

2. A process for recrystallizing the high explosives HMX and RDX in accordance with claim 1, in which the chosen solvent is γ-butyrolactone.

3. A process for recrystallizing the high explosives HMX and RDX in accordance with claim 1, in which the degree of saturation of the lactone-explosive solution, is changed by lowering the temperature.

4. A process for recrystallization of the high explosives HMX and RDX in accordance with claim 3, in which the temperature of the lactone is raised to 110°–120° C. under reduced pressure in order to dissolve the starting explosive crystals and possibly to distill off water and acetic acid, which contaminated the crude explosive, and then to lower the temperature to +20° C.—−10° C.

5. A process for recrystallization of the high explosives HMX and RDX in accordance with claim 1, in which the degree of saturation of the lactone-explosive solution is changed by precipitation with water.

6. A process for recrystallization of the high explosives HMX and RDX in accordance with claim 1, in which the lactone used as the solvent for the recrystallization is recirculated to dissolve more explosive until it has absorbed 8–10% acetic acid from the crude explosive, or has acquired too much water, and after that is repurified by distillation of the acetic acid and water.

7. A process in accordance with claim 1, wherein the crystallization of the explosive is induced by seeding according to standard methods.

8. A process for recrystallizing the high explosives HMX and RDX in accordance with claim 2, in which the degree of saturation of the lactone-explosive solution is changed by lowering the temperature.

9. A process for recrystallization of the high explosives HMX and RDX in accordance with claim 8, in which the temperature of the lactone is raised to 110°–120° C. under reduced pressure in order to dissolve the starting explosive crystals and then to lower the temperature to +20° C.—−10° C.

10. The process of claim 1 wherein said lactone is selected from the group of γ-butyrolactone, γ-valerolactone, δ-valerolactone, and ε-caprolactone.

* * * * *